United States Patent [19]

Jones et al.

[11] Patent Number: 4,697,923

[45] Date of Patent: Oct. 6, 1987

[54] METHOD FOR VISUAL INSPECTION OF MULTILAYER PRINTED CIRCUIT BOARDS

[75] Inventors: Gerald W. Jones, Johnson City; W. Robert Pratt, Binghamton; William J. Summa, Endwell, all of N.Y.

[73] Assignee: IBM Corporation, Armonk, N.Y.

[21] Appl. No.: 843,566

[22] Filed: Mar. 25, 1986

[51] Int. Cl.$^4$ ............................................. G01N 21/88
[52] U.S. Cl. ..................................... 356/239; 356/51; 361/411
[58] Field of Search .......................... 356/237, 239, 51; 361/397, 411

[56] References Cited

U.S. PATENT DOCUMENTS

| | | | |
|---|---|---|---|
| 2,569,793 | 10/1951 | Anderson et al. | 250/86 |
| 3,298,959 | 1/1967 | Marks et al. | 252/300 |
| 3,926,658 | 12/1975 | Cole et al. | 106/287 |
| 4,183,767 | 1/1980 | Kessler | 106/236 |
| 4,365,516 | 12/1982 | Molina | 73/644 |
| 4,392,982 | 7/1983 | Molina | 252/408.1 |
| 4,400,618 | 8/1983 | Bupp et al. | 250/302 |
| 4,538,909 | 9/1985 | Bible et al. | 356/239 X |
| 4,549,206 | 10/1985 | Suzuki et al. | 356/239 X |

OTHER PUBLICATIONS

West et al., "Computer-Controlled Optical Testing of High Density Printed Circuit Boards" 1983, IBM J. Res. Develop. vol. 27, No. 1, pp. 50–58.

*Primary Examiner*—Davis L. Willis
*Assistant Examiner*—Matthew W. Koren
*Attorney, Agent, or Firm*—Perman & Green

[57] ABSTRACT

A method is disclosed for the visual inspection of electrical circuitry deposited in the layers of a multilayer printed circuit board wherein the dielectric layers of the multilayer board are prepared using a clear, light transparent thermosetting resin having incorporated therein a dye which is permeable to visible light but which absorbs light in the 320–440 nm region.

The electrical circuitry in the board can be easily traced by an observer upon illumination of the board by visible light.

5 Claims, No Drawings

METHOD FOR VISUAL INSPECTION OF MULTILAYER PRINTED CIRCUIT BOARDS

BACKGROUND OF THE INVENTION

1. Field of the Invention

The present invention relates to a means for the visual inspection of printed circuit boards. More particularly, the present invention is directed to a means allowing the visual tracing of the electrical circuitry embedded in laminated multilayer printed circuit boards.

2. The Prior Art

In the manufacture of electronic devices, such as computers, printed circuit boards are widely used to support discrete electronic components and to provide the electrical circuitry between the components. Commercial electronic computers have become more powerful since their introduction, yet they have been reduced in physical dimensions from room size to desk size. As their size has descreased and the number of inter-connections due to more powerful logic has increased, the printed circuit boards used have become denser and more complex. Today's printed circuit boards can be extremely dense, with very small geometrics and with many layers.

The printed circuit boards have a central core typically a dielectric material, such as a composite of fiber glass and a thermosetting resin such as an epoxy resin, which core has applied on at least one surface a layer of conductive material such as copper. The layer or layers of conductive material are etched or otherwise processed to provide circuits of predetermined geometrical configuration. The individual circuit boards are then laminated to form a multilayer structure having the etched metal circuitry sandwiched between dielectric layers.

In the event that the multilayer board after it has been laminated requires engineering changes such as deletion of existing internal circuitry, an operator can, by the use of suitable tools make the engineering change. However, in order to perform the engineering change, the operator must trace the circuitry embedded in the multilayer structure from one side of the board to the other in order to find the precise point in the circuitry to perform the engineering change.

A major problem exists in tracing the circuits in multilayer printed circuit boards which are interconnected, for example, by plated through holes where each of the boards in the multilayer structure have one or more circuits on each side of the board and possibly a ground plane, all of which are interconnected to other circuits in other layers in the laminated multilayer boards. Further complicating the tracing of the electrical circuitry is that in past practice, the dielectric layers of the laminated circuit boards have had incorporated therein an opaque dye which is used to aid in inspecting the quality of the circuits using optical automatic inspection systems. For example, in an article entitled "Computer-Controlled Optical Testing of High Density Printed-Circuit Boards" appearing in IBM J. Res. Develop., Vol 27, No. 1, January 1983 pp. 50–58, there is disclosed an inspection method which utilizes a computer-controlled image-detector system which determines circuit imperfections as changes of contrast in reflectivity between the circuitized copper and dielectric layers as it scans only the dielectric or only the circuitized copper portions of the laminate. In operation, the printed circuit board is illuminated by a thallium iodide, high intensity discharge lamp (570 nm). The light is delivered to the board through a fiber optic bundle which is designed to deliver a uniform light at a controlled oblique angle to form a dark field illuminator. An opaque dye is incorporated in the dielectric to provide a high visual contrast using the 570 nm light. The light reflected from the surface under inspection is translated into a video signal the level of which indicates the presence of flaws in the circuitry.

The presence of an opaque dye in the dielectric layers of the multilayer board prevents the transmission of light through these layers. An operator attempting to make an engineering change in this laminated board and tracing circuitry which extends from one side to the opposite side of the board must turn the board over to inspect the opposite side. With opaque dyed boards, the operator frequently loses his place when turning the board over to continue tracing. The loss of the operator's place in addition to being frustrating, is time consuming and thereby adds to the cost of manufacture of the multilayer printed circuit board.

It would therefore be highly advantageous that the multilayer board be transparent to visible light so that an operator tracing the electrical circuitry from one side of the board could complete the tracing without having to turn the board over and thereby avoid the risk of losing his place.

A recent advance in the manufacture of high density multilayer printed circuit boards has eliminated the need for the use of optical inspection systems of the type described above. This latest method is disclosed in U.S. Pat. No. 4,448,804 issued May 15, 1984 to W. J. Amelio at al and assigned to International Business Machines Corporation, the assignee of this invention.

In contrast to prior art processes for selectively metallizing dielectric surfaces used in the manufacture of multilayer printed circuit boards which involve the use of a thin metallic foil, wherein a photoresist is applied and imaged to create spaces where metal deposition can occur, referred to in the art as a "semi-additive" process the method disclosed in U.S. Pat. No. 4,448,804 does not employ a foil for metal deposition. In the method disclosed in U.S. Pat. No. 4,448,804 a collodial activating or seed tin/palladium layer is applied to the roughened dielectric surface and the surface is treated with a suitable photoresist. After developing the imaged resist, the exposed tin/palladium seed acts as a catalyst for electroless deposition whereupon the resist is removed to leave the exposed circuit lines. The method of U.S. Pat. No. 4,448,804 further differs from the semi-additive process in that after metal disposition has been accomplished in the semi-additive process the metal is protected by a solder mask and the resist is stripped leaving the mask on the circuit lines which were formed on a continuous metallic foil. The metallic foil is then etched and the mask removed to leave the desired circuitry.

In dielectric substrates prepared in accordance with the method of U.S. Pat. No. 4,448,804 there is no continuous metal foil on the substrate surface to block the light used to expose the photoresist. Dielectric substrates prepared in accordance with the semi-additive process contained such a foil and prevented the photoresist on the opposite side of the board from being exposed.

Multilayer printed circuit boards manufactured in accordance with the process of U.S. Pat. No. 4,448,804 are not inspected by the computer-controlled inspection system described above, as residual copper is not left between the circuit lines due to the omission of the etch step. In the method disclosed in U.S. Pat. No. 4,448,804 the resist forms a barrier to the plating solution and no shorts are formed and for this reason the presence of an opaque dye in the dielectric layer is not necessary. However, the presence of a dye or dyes which absorb ultraviolet light from 320–440 nm. is still required in the resin system used to produce the laminate as the photoresist deposited on one side of the board must be protected during exposure of the opposite side. Any bleedthrough of ultraviolet radiation will cause the resist to insolubilize in area where it should be removed, thus causing non-continuous lines in the plated circuitry.

The invention of the present application provides a method for the visual inspection of the electric circuitry which has been deposited on the dielectric layers of a multilayer printed circuit board laminate in accordance with the method disclosed in U.S. Pat. No. 4,448,804 and other processes related thereto.

SUMMARY OF THE INVENTION

In accordance with the present invention, there is provided a method for the visual inspection of the electrical circuitry in the layers of a multilayer printed circuit board laminate wherein the planes of the circuitry can be readily traced by visual observation from one side of the laminate, the method comprising forming the multilayer printed circuit board laminate using a dielectric layer comprised of a clear, light transparent thermosetting resin having incorporated therein a dye which is permeable to most visible light but which absorbs light in the 320–440 nanometers (nm) region.

By practicing the method of the present invention in the formation of multilayer printed circuit board laminates, visual inspection of the internal circuit planes of the laminate is readily achieved and the deleterious effect of ultraviolet light on the laminate is avoided. An operator seeking to make an engineering change in the laminated structure can illuminate the multilayer printed circuit board laminate with visible light and trace the embedded electrical circuitry by viewing the circuitry from one side of the board.

DETAILED DESCRIPTION OF THE INVENTION

In preparing the multilayer printed circuit board laminate of the present invention, the dielectric material is prepared by applying to a fiber glass cloth, a solution of a clear, thermosetting resin, such as an epoxy resin, an epoxy novolak, a polyimide, or a phenol-formaldehyde resin. Preferred in the practice of the present invention are brominated epoxy resins which are flame retardant. The thermosetting resin together with a suitable hardener and catalyst is dissolved in a suitable solvent such as methyl ethyl ketone, ethylene glycol monomethyl ether and the like to prepare a liquid system which contains about 20 to about 70 percent by weight of the resin and about 1 to about 5 percent by weight of the hardener and about 0.1 to 0.5 percent by weight of the catalyst.

Also incorporated in the resin solution is about 0.25 to about 1.0 percent by weight of a selective light absorbing dye or a mixture of dyes having the property of absorbing ultraviolet light of 320–440 nm wavelength but being permeable to the passage of visible light. Exemplary of such dyes are dyes marketed under the trademark designation Tinuvin and Uvinul and available from the Ciba-Geigy and GAF Companies respectively. These dyes normally absorb ultraviolet light up to 400 nm. To obtain ultraviolet light absorption in the 400–440 nm region, a yellow dye such as Orasol Yellow or a fluorescent dye such as Fluorescent Yellow G available from Morton Norwich is admixed with Tinuvin or Uvinul type dyes to obtain light absorbency over the entire 320–440 nm range. These dyes when incorporated in the clear thermosetting resin and the resin is cured, permit the cured resin to be sufficiently transparent so that a plurality of the dielectric layers formed using the dyed resin can be visually inspected when the multilayer printed circuit board is illuminated with an ordinary visible light source.

In preparing multilayer laminated circuit boards following the practice of the present invention, a prepreg is prepared by applying to the surface of a fiber glass sheet, by any suitable means, such as brushing, dipping or spraying, a solution of a clear, transparent thermosetting resin containing the selective light absorbent dye of the present invention. The fiber glass sheet impregnated with the resin solution is then placed in an oven at a temperature of about 125° to about 150° C. for about 3 to about 5 minutes to remove the solvent and partially cure the resin impregnated on the surface of the fiber glass sheet. The fiber glass sheet containing the partially cured resin is then placed between copper sheets and heated to about 150° to about 180° C. under 200 to about 700 psi pressure to form a core member for the multilayer printed circuit board. The copper layers are circuitized by conventional practice such as the method of U.S. Pat. No. 4,448,804 to prepare a printed circuit pattern. Dielectric layers comprised of a similar resin impregnated fiber glass sheet are assembled between the metallized printed circuit layers of the core member to form an assembly. A plurality of these assemblies are stacked and cured in such a manner whereby the sheets of the assemblies coalesce with respect to each other to form a monolithic multilayer structure having inner metallized printed circuit layers embedded in the coalesced dielectric layers. Appropriate conductive vias are provided between all layers in a manner known to those skilled in the art. Typical parameters for effecting the coalescence of the assembled layers to prepare the multilayer printed circuit board laminate are 300° to 350° F. at 450 to 550 psi for approximately 0.75 to 1.5 hours.

In an example of the practice of the present invention a 24"×28" multilayer printed circuit board having a thickness of 15 mils and containing 2 layers of circuitry prepared in accordance with the process of U.S. Pat. No. 4,448,804 and deposited on a brominated epoxy resin/fiber glass composite was prepared. The brominated epoxy resin had incorporated therein a mixture of dyes composed of 0.4% by weight Tinuvin and 0.4% by weight Fluorescent Yellow G. When viewed from an illuminated source behind the board, such as a light table or microscope an observer could see through the internal layers of the printed circuit board and could readily trace the circuitry by viewing one side of the board.

In addition to being able to readily trace the circuitry, the tin/palldium seeder coverage on the epoxy glass composite could be easily visualized to verify the uniformity of the seeder deposit. In the process of U.S. Pat. No. 4,448,804 seeder uniformity is essential so that defects in the circuitry are not produced during electroless plating. Too little seed can lead to poor plating and circuitry with non-continuous lines. Too much seeder can produce nodules and lead to shorts due to incomplete removal, causing dendritic growth under certain humidity and voltage conditions.

The visualization of seeder uniformity is not possible if a dark colored or opaque dye is incorporated in the epoxy glass composite. The tin/palladium seeder used in the process of U.S. Pat. No. 4,448,804 is brown-black and cannot be seen against the dark background. The presence in the epoxy/glass composite of light permeable dyes permits inspection of the dark seeder deposit.

The incorporation of a fluorescent dye such as Fluorescent Yellow G in the epoxy/glass composite causes the board to fluoresce when viewed under ultra violet light. This property permits the detection of any contamination which absorbs UV light on the board surface, the contamination appearing dark against the fluorescent yellow background.

Dark laser markings applied to the epoxy/glass composite to keep track of the laminate through the various processing steps are not legible when a dark background is used. However, by using a light colored or clear laminate, in accordance with the present invention such dark laser markings can be easily read. Laser marking involves transferring enough laser energy to the laminate to char the resin. The charred resin is then visible as black lettering on a light background.

While specific components of the present system are defined above, many other variables may be introduced which may in any way affect, enhance, or otherwise improve the system of the present invention. These are intended to be included herein.

Although variations are shown in the present application, many modifications and ramifications will occur to those skilled in the art upon a reading of the present disclosure. These, too, are intended to be included herein.

We claim:

1. A method for the visual inspection of the electrical circuitry embedded in the layers of a multilayer printed circuit board which comprises:
    preparing the multilayer printed circuit board from a composite of circuitized metal and dielectric layers, the dielectric layers being formed using a clear, light transparent thermosetting resin having incorporated therein a selective light absorbing dye having the property of absorbing ultaviolet light of 320 to 440 nm wavelength and permeable to the passage of visible light; and
    exposing the multilayer printed circuit board to a source of visible light to permit visual inspection of the board.

2. The method of claim 1 wherein the thermosetting resin is an epoxy resin.

3. The method of claim 1 wherein the dielectric layer is formed from a composite of a thermosetting resin and a fiber glass sheet.

4. The method of claim 3 wherein the thermosetting resin is an epoxy resin.

5. The method of claim 1 wherein the dye is incorporated in the thermosetting resin at a concentration of about 0.5 to about 1.0% by weight.

* * * * *